United States Patent [19]

Petty

[11] 4,424,392

[45] Jan. 3, 1984

[54] ALDEHYDE CONTAINING HYDROLYZABLE SILANES

[75] Inventor: Herbert E. Petty, Bethel, Conn.

[73] Assignee: Union Carbide Corporation, Danbury, Conn.

[21] Appl. No.: 361,189

[22] Filed: Mar. 24, 1982

[51] Int. Cl.$^3$ ............................ C07F 7/04; C07F 7/18
[52] U.S. Cl. .................................... 556/436; 556/440
[58] Field of Search ................................ 556/436, 440

[56] References Cited

U.S. PATENT DOCUMENTS

| | | | |
|---|---|---|---|
| 2,588,083 | 3/1952 | Burkhard et al. | 556/436 |
| 2,641,605 | 6/1953 | Frisch et al. | 556/436 |
| 2,803,637 | 8/1957 | Speier | 556/436 |
| 2,805,236 | 9/1957 | Kiffer et al. | 556/436 |
| 2,989,559 | 6/1961 | Marsden | 556/436 |
| 3,099,670 | 7/1963 | Prober | 556/436 X |
| 3,168,553 | 2/1965 | Slaugh | 260/497 |
| 3,527,809 | 9/1970 | Pruett et al. | 260/604 |
| 3,824,278 | 7/1974 | Galantay | 556/436 X |
| 4,002,651 | 1/1977 | Marsden et al. | 260/349 |

OTHER PUBLICATIONS

"J. of General Chemistry" of the USSR (A Translation of Zhurnal Obshchei Khimi, pp. 1395–1397, Dec. 20, 1977), vol. 47, No. 7, Part 1, Jul. 1977 Article, Carbonylation of Trimethylvinylsilane, by L. V. Morozova et al.
"J. Org. Chem.", vol. 17, pp. 1107–1109, (1952), Article, Organosilicon Aldehydes, by C. A. Burkhard et al.
"J. Org. Chem.", vol. 35, No. 12, pp. 4180–4183, (1970), Article, Preparations and Reactions of Siloxanylpropanols, by W. E. Dennis et al.
"Ind. and Eng. Chem.", vol. 58, No. 3, Mar. 1966, pp. 33–37, Article, Silane Coupling Agents, by S. Sterman et al.
"Ind. Eng. Chem. Prod. Res. Dev.", vol. 17, No. 3, 1978, pp. 205 to 207, Article, Low-Pressure Hydroformylation of Methyl Oleate with an Activated Rhodium Catalyst, by J. P. Friedrich.
"Zhurnal Obshchei Khimi", vol. 51, No. 10, pp. 2266–2270, Oct. 1981, Artical, Hydroformylation and Carbonylation of Olefins In the Presence of Stannylene Complexes of Metal Carbonyls, by G. I. Magomedov et al.

*Primary Examiner*—Paul F. Shaver
*Attorney, Agent, or Firm*—Eugene C. Trautlein

[57] ABSTRACT

Aldehyde containing hydrolyzable silane compositions of matter and a process for preparing same by hydroformylating an ethylenically unsaturated organic containing hydrolyzable silane.

25 Claims, No Drawings

ALDEHYDE CONTAINING HYDROLYZABLE SILANES

BRIEF SUMMARY OF THE INVENTION

1. Technical Field

This invention is directed to novel aldehyde containing hydrolyzable silane compositions of matter and their uses, as well as to a process for producing same. More particularly this invention is directed to hydrolyzable silane compositions of matter containing an aldehyde radical and to a hydroformylation process for producing same. Said process involves the hydroformylation of an ethylenically unsaturated organic containing hydrolyzable silane starting material with carbon monoxide and hydrogen in the presence of a Group VIII metal catalyst to produce the novel aldehyde containing hydrolyzable silane compositions of this invention which have beneficial utility as coupling agents to enhance the adhesion of a broad variety of substrates and polymers as well as being useful as starting materials for the production of hydroxy substituted organic containing hydrolyzable silanes via hydrogenation.

2. Background Art

While a tremendous amount of prior art exists concerning the hydroformylation (an OXO reaction) of ethylenically unsaturated organic compounds, such as olefins, with carbon monoxide and hydrogen (synthesis gas) in the presence of a Group VIII metal catalyst such as cobalt and rhodium, no prior art has been found utilizing this reaction to convert ethylenically unsaturated organic containing hydrolyzable silanes to their aldehyde containing silane composition counterparts.

The "Journal of General Chemistry" of the USSR (a translation of "Zhurnal Obshchei Khimi," pp 1395–1397, Dec. 20, 1977) Vol. 47, Number 7, Part 1, July 1977 contains an article entitled "Carbonylation of Trimethylvinylsilane" by L. V. Morozova et al. which discloses hydroformylating trimethylvinylsilane in the presence of a rhodium catalyst to produce trimethylsilylpropionaldehydes. However said article is silent with regard to the carbonylation or hydroformylation of hydrolyzable silanes.

The "J. Org. Chem." Vol. 17, pp 1107–1109 (1952) contains the article entitled "Organosilion Aldehydes" by C. A. Burkhard et al. disclosing reacting allyltrimethylsilane with carbon monoxide and hydrogen in the presence of a cobalt catalyst to produce silicon-containing aldehyde. However said article is silent with regard to the subject of aldehyde containing hydrolyzable silanes.

The "J. Org. Chem.", Vol. 35, No. 12, pp 4180–4183 (1970) contains an article entitled "Preparation and Reactions of Siloxanylpropanols" by W. E. Dennis et al. disclosing the hydrolysis of alkoxy substituted alkyl containing disiloxane to produce propionaldehyde containing disiloxane and refers to the addition of trimethoxysilane to acrolein dimethylacetal to give 3,3-dimethoxypropyltrimethoxysilane indicating that alkoxysilanes as well as disiloxanes can be used as aldehyde precursors. However, no aldehyde containing hydrolyzable silanes nor a suitable method for their production are seen disclosed in said article.

DISCLOSURE OF THE INVENTION

It has now been discovered that novel aldehyde containing hydrolyzable silanes having the formula

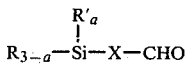

wherein R represents a hydrolyzable radical selected from the class consisting of alkoxy and aryloxy radicals, wherein R' represents a monovalent hydrocarbon radical, wherein X represents a divalent organic bridging group and wherein a has a value of 0 to 2, can be prepared by hydroformylating a hydrolyzable alkoxy silane having the formula

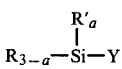

wherein R, R' and a are the same as defined above and Y represents an ethylenically unsaturated organic radical. Moreover the novel aldehyde containing silane compositions of this invention have the advantage of being soluble in water and/or alcoholic solvents thus rendering them especially suitable as coupling agents in foundry resins for core strength improvements and in the glass finishing industry.

Accordingly it is an object of this invention to provide novel aldehyde containing hydrolyzable silane compositions of matter. It is another object of this invention to provide a hydroformylation process for producing said silane compositions of matter. Other objects and advantages of this invention will become readily apparent from the following description and appended claims.

DETAILED DESCRIPTION

As noted above the aldehyde containing hydrolyzable silane compositions of matter of this invention are those having the formula

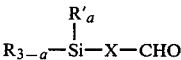

wherein R represents a hydrolyzable group selected from the class consisting of alkoxy and aryloxy radicals, R' represents a monovalent hydrocarbon radical, X represents a divalent organic bridging group and a has a value of 0 to 2, preferably 0 or 1.

As further noted above, the aldehyde containing hydrolyzable silane compositions of matter of this invention can be prepared by the hydroformylation process of this invention which comprises hydroformylating a hydrolyzable silane starting material having the formula

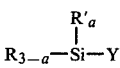

wherein R, R' and a are the same as defined above and wherein Y represents an ethylenically unsaturated organic radical, with carbon monoxide and hydrogen in the presence of a Group VIII metal catalyst.

Illustrative hydrolyzable radicals represented by R in the above silane formulas include alkoxy and aryloxy radicals having from 1 to 12 carbon atoms, e.g. alkoxy radicals (such as methoxy, ethoxy, propoxy, isopropoxy, dodecyloxy, 2-methyethoxy, and the like), and aryloxy radicals such as phenoxy, naphthyloxy, biphenyloxy, and the like). Preferably R is a lower alkoxy radical of 1 to 4 carbon atoms, especially methoxy or ethoxy.

Illustrative monovalent hydrocarbon radicals that may be represented by R' in the above silane formulas include such radicals as alkyl (e.g. methyl, ethyl, propyl, pentyl, dodecyl, and the like); cycloalkyl as cyclobutyl cyclohexyl), and the like; aryl (such as phenyl, naphthyl, biphenyl, and the like); alkaryl (such as 4-methylphenyl, 2,4-diethylphenyl, and the like); arylalkyl (such as benzyl, betaphenylethyl, and the like); and the like. Preferably, the monovalent hydrocarbon radical is a member selected from the group consisting of phenyl and lower alkyl radicals of 1 to 4 carbon atoms, especially a methyl radical.

Illustrative ethylenically unsaturated organic radicals represented by Y in the above silane starting material formula include ethylenically unsturated straight-chain, branch-chain and cyclic radicals containing from 2 to 20 carbon atoms. Such unsaturated radicals can be characterized by a terminal or internal ethylenic group and may contain groups or substituents which do not essentially interfere with the course of the hydroformylation reaction of this invention. Such groups or substituents can be illustrated by carbonyl $$-\overset{O}{\underset{\|}{C}}-), \text{ oxycarbonyl } (-\overset{O}{\underset{\|}{OC}}-),$$

oxy (—O—), alkoxy, phenyl and the like. The more preferred ethylenically unsaturated radicals containing from 2 to 20 carbon atoms include alkenes, such as —CH=CH$_2$, —CH$_2$CH=CH$_2$, —CH=CHCH$_3$, —CH$_2$CH=CHCH$_3$, —CH$_2$CH$_2$CH=CH$_2$, —CH$_2$CH$_2$C(CH$_3$)=CH$_2$, —CH$_2$CH=C(CH$_3$)CH$_3$, —CH$_2$CH(CH$_3$)CH=CH$_2$, —CH$_2$C(CH$_3$)=CHCH$_3$, —(CH$_2$)$_3$CH=CH$_2$, —(CH$_2$)$_4$CH=CH$_2$, —(CH$_2$)$_5$CH=CH$_2$, —(CH$_2$)$_6$CH=CH$_2$, —(CH$_2$)$_8$CH=CH$_2$, —(CH$_2$)$_{16}$CH=CH$_2$, —(CH$_2$)$_{18}$CH=CH$_2$, —CH$_2$CH(C$_2$H$_5$)(CH$_2$)$_3$CH=CH$_2$, etc.; alkylene alkenyl ethers, such as ethyleneoxyvinyl (—C$_2$H$_4$OCH=CH$_2$), ethyleneoxyallyl (—C$_2$H$_4$OCH$_2$CH=CH$_2$), propyleneoxyvinyl (—C$_3$H$_6$OCH=CH$_2$), propyleneoxyallyl (—C$_3$H$_6$OCH$_2$CH=CH$_2$), etc.; alkylene alkenoates, such as propylenemethylmethacrylate $$\overset{OCH_3}{\underset{\|}{(-C_3H_6OCC=CH_2,}}$$

etc.; and cycloalkenes, such as cyclohexenyl

, ethylenecyclohexenyl

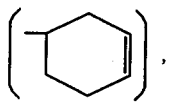, bicycloheptenyl

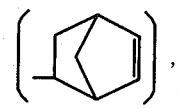, etc.; and the like. The most preferred ethylenically unsaturated radicals are alkenes containing from 2 to 6 carbon atoms, especially vinyl.

Illustrative divalent organic radicals represented by X in the above aldehyde containing silane formula obviously correspond to the ethylenically unsaturated organic Y radical of the silane starting material of the hydroformylation process of this invention after addition of the aldehyde (—CHO) group to the unsaturated portion of said Y radical and therefore include divalent organic radicals containing 2 to 20 carbon atoms which may be straight-chain, branch-chain or cyclic radicals in which the aldehyde group (CHO) is bonded to a terminal or internal carbon atom and which may further contain groups or substituents which do not essentially interfere with the course of the hydroformylation reaction of this invention such as those described above for the Y radical of the silane starting material. The more preferred divalent organic bridging groups represented by X include alkylene radicals, such as

—CH$_2$CH$_2$—, —ĊHCH$_3$, —CH$_2$CH$_2$CH$_2$—, —CH$_2$ĊHCH$_3$,

—ĊCH$_2$CH$_3$, —CH$_2$CH$_2$ĊHCH$_3$, —CH$_2$ĊHCH$_2$CH$_3$,

—(CH$_2$)$_4$—, —CH$_2$CH$_2$C(CH$_3$)CH$_2$—, —CH$_2$CH$_2$Ċ(CH$_3$)$_2$,

—CH$_2$ĊHCH(CH$_3$)$_2$, —CH$_2$CH(CH$_3$)CH$_2$CH$_2$—,

—CH$_2$CH(CH$_3$)ĊHCH$_3$, —CH$_2$Ċ(CH$_3$)CH$_2$CH$_3$, —(CH$_2$)$_5$—,

—(CH$_2$)$_3$ĊHCH$_3$, —(CH$_2$)$_6$—, —(CH$_2$)$_4$ĊHCH$_3$, —(CH$_2$)$_7$—,

—(CH$_2$)$_5$ĊHCH$_3$, —(CH$_2$)$_8$—, —(CH$_2$)$_6$ĊHCH$_3$, —(CH$_2$)$_{10}$—,

—(CH$_2$)$_8$ĊHCH$_3$, —(CH$_2$)$_{18}$—, —(CH$_2$)$_{16}$ĊHCH$_3$, —(CH$_2$)$_{20}$—,

—(CH$_2$)$_{18}$ĊHCH$_3$, —CH$_2$CH(C$_2$H$_5$)(CH$_2$)$_3$—,

—CH$_2$CH(C$_2$H$_5$)(CH$_2$)$_3$ĊHCH$_3$, etc.;

alkyleneoxyalkylene radicals, such as —C$_2$H$_4$OC$_2$H$_4$—,

—C$_2$H$_4$OĊHCH$_3$, —C$_2$H$_4$O(CH$_2$)$_3$—, —C$_2$H$_4$OCH$_2$ĊHCH$_3$,

—C$_3$H$_6$OC$_2$H$_4$—, —C$_3$H$_6$OĊHCH$_3$, —C$_3$H$_6$OC$_3$H$_6$—,

—C₃H₆OCH₂CHCH₃ etc.; alkylene —OC(=O)—alkylene radicals, such as 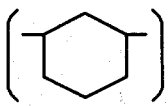, —C₃H₆OC(=O)C(CH₃)₂, etc. and
            |
            OCH₃ cycloalkylene radicals, such as 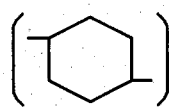,

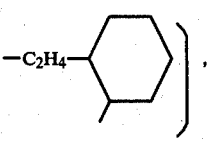,

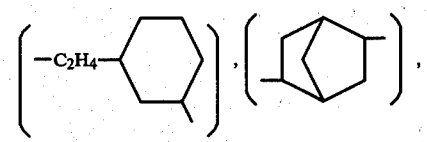,

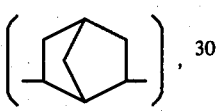, etc., and the like. The most preferred divalent organic bridging groups are alkylenes containing from 2 to 6 carbon atoms, especially ethylene.

Such hydrolyzable silane starting materials of the hydroformylation process of this invention and/or methods for their preparation are well known in the art. Among the more preferred hydrolyzable silanes are those having the formula (CH₃O)₃SiCH=CH₂

(CH₃O)₃SiCH₂CH=CH₂

(C₂H₅O)₃SiCH=CH₂

(C₂H₅O)₃SiCH₂CH=CH₂

(CH₃OCH₂CH₂O)₃SiCH=CH₂

(CH₃OCH₂CH₂O)₃SiCH₂CH=CH₂

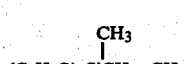

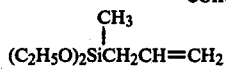

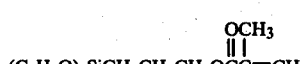

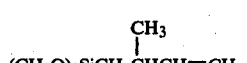

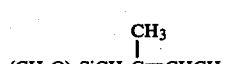

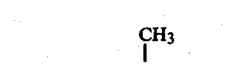

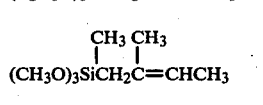

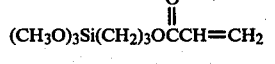

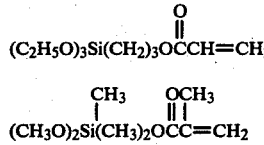

(CH₃O)₃Si(CH₂)₃OC(=O)CH=CH₂

(C₂H₅O)₃Si(CH₂)₃OC(=O)CH=CH₂

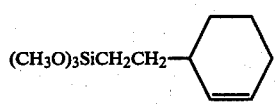

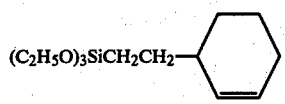

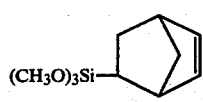

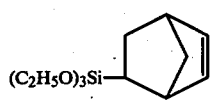

and the like.

Of course it is to be understood that, as in the case with the conventional hydroformylation of any olefinic compound, the aldehyde containing silane compositions of matter of this invention are produced as mixtures of isomeric aldehyde containing silanes due to the two possible aldehyde addition sites of the ethylenically unsaturated radical Y of the silane starting material of the hydroformylation process of this invention.

Thus among the more preferred aldehyde containing silane compositions of matter of this invention are those silanes having the formula (CH₃O)₃SiCH₂CH₂CHO -continued (CH₃O)₃SiCHCH₃
       |
       CHO (CH₃O)₃SiCH₂CH₂CH₂CHO (CH₃O)₃SiCH₂CHCH₃
            |
            CHO CH₃
      |
(CH₃O)₂SiCH₂CH₂CHO CH₃
      |
(CH₃O)₂SiCHCH₃
       |
       CHO CH₃
      |
(CH₃O)₂SiCH₂CH₂CH₂CHO CH₃
      |
(CH₃O)₂SiCH₂CHCH₃
            |
            CHO (C₂H₅O)₃SiCH₂CH₂CHO (C₂H₅O)₃SiCHCH₃
         |
         CHO (C₂H₅O)₃SiCH₂CH₂CH₂CHO (C₂H₅O)₃SiCH₂CHCH₃
             |
             CHO CH₃
      |
(C₂H₅O)₂SiCH₂CH₂CHO CH₃
      |
(C₂H₅O)₂SiCHCH₃
        |
        CHO CH₃
      |
(C₂H₅O)₂SiCH₂CH₂CH₂CHO CH₃
      |
(C₂H₅O)₂SiCH₂CHCH₃
             |
             CHO OCH₃
            ‖ |
(CH₃O)₃SiCH₂CH₂CH₂OCCHCH₂CHO OCH₃
            ‖ |
(CH₃O)₃SiCH₂CH₂CH₂OCCCH₃
                    |
                    CHO OCH₃
            ‖ |
(C₂H₅O)₃SiCH₂CH₂CH₂OCCHCH₂CHO OCH₃
            ‖ |
(C₂H₅O)₃SiCH₂CH₂CH₂OCCCH₃
                     |
                     CHO CH₃
        |
(CH₃O)₃SiCH₂CHCH₂CH₂CHO -continued CH₃
          |
(CH₃O)₃SiCH₂CHCHCH₃
               |
               CHO (CH₃OCH₂CH₂O)₃SiCH₂CH₂CHO (CH₃OCH₂CH₂O)₃SiCHCH₃
                |
                CHO (CH₃OCH₂CH₂O)₃SiCH₂CH₂CH₂CHO (CH₃OCH₂CH₂O)₃SiCH₂CHCH₃
                    |
                    CHO CH₃
         |
(CH₃OCH₂CH₂O)₂SiCH₂CH₂CHO CH₃
         |
(CH₃OCH₂CH₂O)₂SiCHCH₃
                |
                CHO CH₃
         |
(CH₃OCH₂CH₂O)₂SiCH₂CH₂CH₂CHO CH₃
         |
(CH₃OCH₂CH₂O)₂SiCH₂CHCH₃
                    |
                    CHO (CH₃O)₃Si—CH₂CH₂—⟨cyclohexyl⟩—CHO (CH₃O)₃Si—CH₂CH₂—⟨cyclohexyl⟩—CHO (C₂H₅O)₃Si—CH₂CH₂—⟨cyclohexyl⟩—CHO (C₂H₅O)₃Si—CH₂CH₂—⟨cyclohexyl⟩—CHO (CH₃O)₃Si—⟨norbornyl⟩—CHO (CH₃O)₃Si—⟨norbornyl⟩—CHO -continued

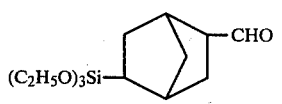

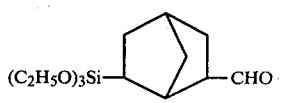

and the like.

The hydroformylation process of this invention may thus be illustrated by the general equation

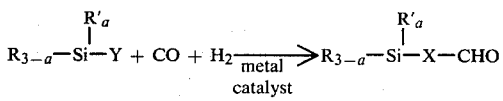

wherein R, R', Y, X and a are the same as defined above, and more particularly by the specific equation $$(C_2H_5O)_3SiCH=CH_2 + CO + H_2 \xrightarrow[\text{catalyst}]{\text{metal}}$$

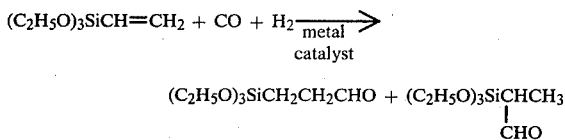

Any conventional hydroformylation procedure heretofore employed in converting organic olefin compounds to their corresponding aldehyde counterparts may be employed in this invention.

For instance the metal catalyst employed in the present invention may be any conventional Group VIII transition metal hydroformylation catalyst selected from the group consisting of cobalt, ruthenium, rhodium, iridium, etc., the more common and preferred metal catalysts being cobalt or rhodium catalysts. In general it is recommended to employ a rhodium hydroformylation catalyst in the present invention because of their ability to function well under mild reaction conditions. Such Group VIII transition metal hydroformylation catalysts are well known in the hydroformylation art and in their active form are in a reduced metal valance state. Moreover such metal catalysts are often complexed with a suitable organic ligand, e.g. an organophosphorus compound such as a triorganophosphine or triorganophosphite ligand. In the present invention excellent results have been obtained by employing a rhodium or alumina catalyst. Such supported rhodium metal catalysts and a simple method for preparing and activating same are disclosed e.g. in the article by J. P. Friedrich, "Ind. Eng. Chem. Prod. Res. Dev.", Vol. 17, No. 3, 1978, page 205. Of course it is obvious that the amount of metal catalyst employed need only be a catalytic amount, i.e. an amount sufficient to catalyze the hydroformylation process. In general the optimum catalyst concentration in the hydroformylation reaction medium will obviously depend upon the concentration of the silane starting material to be hydroformylated and the rate of reaction desired, the most optimum concentrations of course being easily determinable by routine experimentation.

It is to be further understood that, as taught in the case of conventional hydroformylation processes to produce aldehydes from organic olefins, the process of this invention, if desired, may also be carried out in the presence of any suitable solvent and/or free organic ligand, i.e. excess ligand that is not complexed with the metal catalyst.

The hydroformylation process of this invention may be carried out under such reaction conditions at temperatures of from about 50° C. to about 200° C., preferably from about 60°–110° C., total gas pressures of from 1 to about 700 atmospheres preferably from about 5 to 100 atmospheres; and ratios of hydrogen gas to carbon monoxide gas of from about 10:1 to about 1:10, preferably from about 3:1 to about 1:3. In general it is most preferred to employ about a 1:1 mole ratio of hydrogen gas to carbon monoxide gas. Of course it is to be understood that it is preferred to avoid the presence of any conventional hydroformylation metal catalyst poisons, such as halogen and sulfur, in the reaction medium that would have an undue adverse effect on the desired result of the reaction. Moreover, the hydroformylation process of this invention may be conducted in any suitable sealed, stirred (or rocking) vessel, such as an autoclave, of conventional construction. Likewise, it is further obvious that the most preferred operating conditions of a given process of the present invention can be easily and readily determined by routine experimentation.

As noted above mixtures of the aldehyde containing hydrolyzable silanes of this invention, i.e. silanes wherein the aldehyde group (CHO) is bonded to the alpha carbon atom of the ethylenic group of the unsaturated radical of the silane starting material, i.e. that ethylenic carbon atom farthest removed from the silicon atom, e.g. $(CH_3O)_3SiCH_2CH_2CHO$, and silanes wherein the aldehyde group (CHO) is bonded to the beta carbon atom of the ethylenic group of the unsaturated radical of the silane starting material, i.e. the ethylenic carbon atom closest to the silicon atom, e.g.

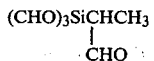

are produced by the hydroformylation process of this invention. Such aldehyde containing silane compounds have been readily separated and identified by Infrared (IR) spectroscopy, gas chromatograph/mass spectroscopy and nuclear magnetic resonance (n m r) spectroscopy. The ratio of such aldehyde containing silane isomers in said product mixtures is immaterial to the present invention and may vary from about 1 to 99 percent by weight of alpha type produced aldehyde containing silane (e.g. silanes containing a straight-chain aldehyde radical) and from about 99 to 1 percent by weight of beta type produced aldehyde containing silane (e.g. silanes containing a branch-chain aldehyde radical), since it is not necessary nor preferred to separate both types of silanes prior to their use as coupling agents although such separation may be possible, e.g. by preparative gas chromatography.

Moreover in addition to producing the above described mixtures of the aldehyde containing silanes of this invention it has been been further surprisingly found to also produce at the same time novel siloxa-cyclic compounds when certain silane starting materials have been employed. These siloxa-cyclic compounds which may be identified by gas chromatography/mass spectroscopy and nuclear magnetic resonance (nmr) spectroscopy are believed to arise from the enol form of the aldehyde group of the silane product displacing one of the hydrolyzable radicals of the silane to produce siloxa-cyclic (or cyclic silyl ether) compound counterparts of the general formula

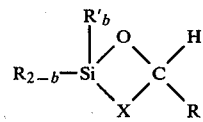

wherein R, R' and X are the same as defined above and b has a value of 0 or 1.

It is to be noted however that while such siloxa-cyclic compounds having the above formula wherein R is a methoxy or ethoxy radical, R' is methyl, X is a divalent alkylene radical selected from the group consisting of

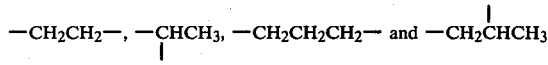

radicals and b has a value of 0 or 1 have been observed in the production of aldehyde-ethylene and aldehyde-propylene containing silane products, corresponding siloxa-cyclics were not observed in the production of aldehyde-propylene methylmethacrylate containing silanes. Such leads one to speculate that such siloxa-cyclic compounds may not be formed if the ethylenically unsaturated radical of the silane starting material to be hydroformylated is excessively long or is already contained in a cycloalkenyl radical because of possible steric interference. In any event such siloxa-cyclic compounds are novel compositions of matter and may constitute from 0 up to about 25 percent by weight or higher of the hydroformylation reaction product produced by the hydroformylation process of this invention.

Moreover such siloxa-cyclic compounds have not been found to be detrimental to the use of the aldehyde containing silane product compositions of matter of this invention and need not be removed prior to use of the aldehyde containing silanes. Indeed it is speculated that when the aldehyde containing silanes are hydrolyzed and/or employed as coupling agents that any such siloxa-cyclic compounds that may be present revert back into the corresponding aldehyde containing silanes from which they are believed to have been derived and/or function in the same manner as said aldehyde containing silanes.

The aldehyde containing silane compositions of matter of this invention even in their crude product mixture form can be used as intermediates to produce hydroxy substituted organic containing hydrolyzable silanes. More particularly such aldehyde containing silane compositions of matter are especially useful as hydrolyzable silane coupling agents in the foundry resin and glass finishing industries. The use of silane coupling agents to promote the adhesion of various substrates with a broad variety of polymers is well known in the art and the aldehyde containing hydrolyzable silanes of this invention can be employed in the same manner as previous conventional silane coupling agents such as taught e.g. by U.S. Pat. No. 4,002,651, the disclosure of which is incorporated herein by reference thereto. For instance the preferred aldehyde containing silane compositions of matter of this invention are readily soluble in water rendering them especially suitable for use as size binders in the glass finishing industry.

The following examples are illustrative of the present invention and are not to be regarded as limitative. It is to be understood that all the parts, percentages and proportions referred to herein and in the appended claims are by weight unless otherwise noted.

EXAMPLE 1

Into a clean, dry, 300 ml stainless steel reactor was added: 75 g (0.4 mole) of vinyltriethoxysilane; 0.75 g triphenylphosphite; and 0.75 g of activated rhodium catalyst, i.e. 5% rhodium supported on alumina (Rh/Al$_2$O$_3$) which was prepared by heating commercial 5% Rh/Al$_2$O$_3$ at 600° C. in the presence of air for three hours, as described by J. P. Friedrich, *Ind. Eng. Chem. Prod. Res. Dev.*, Vol. 17, No. 3, 1978, p. 205. The autoclave was sealed, flushed 5 times with nitrogen and 5 times with a 1:1 hydrogen/carbon monoxide mixture. The hydrogen-carbon monoxide mixture was supplied to the reactor from a 2 liter high pressure reservoir via a pressure regulator in order to maintain a constant pressure at the reactor and also conveniently monitor the consumption of hydrogen and carbon monoxide by the reaction. The pressure on the autoclave was adjusted to 180 psi and the reactor was heated to 80° C. with agitation. At 80° C., gas uptake was extremely rapid as witnessed by the drop in pressure at the reservoir and concomitant exothermic reaction increased the temperature of the contents reactor to 105° C. Uptake of gas was essentially complete after 15 minutes. The reaction was maintained at 90±10° C. for two hours at 200 psi H$_2$/CO to ensure reaction completion. After cooling, about 85.4 grams of liquid reaction product was collected and filtered of catalyst residue and then analyzed.

Gas chromatography, infrared analysis, carbon-13 and proton nuclear magnetic resonance spectroscopy and gas chromatography/mass spectroscopy of said liquid reaction product proved the absence of starting vinyltriethoxy silane and confirmed that the liquid reaction product consisted essentially of (a) about 81 percent by weight of an aldehyde containing silane having the formula (C$_2$H$_5$O)$_3$SiCH$_2$CH$_2$CHO infrared carbonyl band 5.84 microns; proton nmr absorption (triplet, 1, hydrogen) at 9.75 ppm downfield from (CH$_3$)$_4$Si and a carbon-13 nmr absorption for the aldehyde (CHO) group at 200.91 ppm downfield from (CH$_3$)$_4$Si; (b) about 3 percent by weight of an aldehyde containing silane having the formula

mass spectral molecular ion (M) of 220 and its fragmentation pattern exhibiting the presence of a aldehyde (CHO) group; and (c) about 16 percent by weight of a siloxa-cyclic compound having the formula

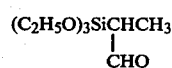

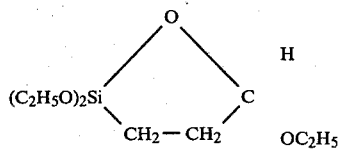

mass spectral molecular ion (M) of 220; carbon-13 nmr absorption for the methine (CH) carbon group at 98.9 ppm downfield from (CH₃)₄Si and no infrared carbonyl band absorption.

EXAMPLE 2

Following a procedure outlined in Sandler and Karo *Organic Functional Group Preparations*, Vol. III, pp. 1–75, Academic Press, N.Y., 1972, for the acid catalyzed reaction of aldehydes with orthoformates to produce acetals, a portion of the reaction product of Example 1 was mixed with an equimolar amount of triethylorthoformate in ethanol solvent and NH₄Cl as catalyst and heated for 2½ hours at reflux. The solvent was removed by flash distillation and the product was distilled 82° C. and 1 mm Hg to yield a two component product mixture of about 95 percent by weight of

(C₂H₅O)₃SiCH₂CH₂CH(OC₂H₅)₂ and about 5 weight percent of

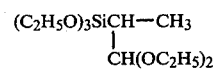
(C₂H₅O)₃SiCH—CH₃
         |
         CH(OC₂H₅)₂ which was found to be identical in all respects with a gas chromatography/mass spectroscopy and nmr analyzed two component mixture of the same above depicted acetal functional silanes prepared by reacting triethoxysilane and acrolein dimethylacetal following the procedure of Dennis and Ryan "J. of Organic Chemistry", Vol. 36, No. 12, pages 4180–4183 which further chemically verifies the aldehyde containing silane products of Example 1.

EXAMPLE 3

Following the procedure of Example 1, vinylmethyldiethoxysilane 160.3 g. (1 mole), 0.8 g. triphenylphosphite, 0.8 g. of activated 5% Rh/Al₂O₃ catalyst (prepared as described in Example 1) were placed in a 300 cc rocking type autoclave. After sealing and purging, the reactor was pressurized to 200 psi with a 1:1 H₂/CO gas mixture from a two liter gas reservoir and heated with rocking. After 12 hours at 120° C. (with observable heat liberated raising the temperature to 140° C.) a pressure drop in the reservoir of 190 lbs/in² was noted. After cooling, 178.3 g. of liquid reaction product was ollected and filtered. Gas chromatography, infrared analysis, carbon-13 and proton nuclear magnetic resonance spectroscopy and gas chromatograph/mass spectroscopy of said liquid reaction product indicated about a 98% conversion of the vinylmethyldiethoxysilane starting material and confirmed that the liquid reaction product consisted essentially of (a) about 73 percent by weight of

        CH₃
         |
(C₂H₅O)₂—SiCH₂CH₂CHO (b) about 8 percent by weight of

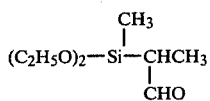
            CH₃
             |
(C₂H₅O)₂—Si—CHCH₃
             |
            CHO and (c) about 19 percent by weight of

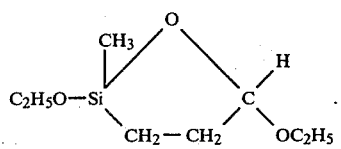

EXAMPLES 4–29

Following the procedure of Example 1, various vinyl silanes were hydroformylated under varying operating parameters to produce varying mixtures of aldehyde containing silane product compositions of matter. The hydroformylation of vinyltriethoxysilane produced a silane product mixture of (C₂H₅O)₃SiCH₂CH₂CHO (the normal isomer),

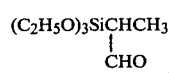
(C₂H₅O)₃SiCHCH₃
         |
         CHO (the branch isomer) and

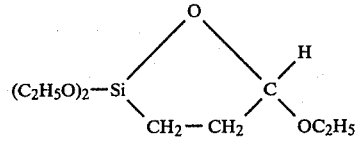

(the siloxa-cyclic). The hydroformylation of vinyltrimethoxysilane produced a silane product mixture of (CH₃O)₃SiCH₂CH₂CHO (the normal isomer),

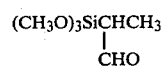
(CH₃O)₃SiCHCH₃
         |
         CHO (the branch isomer), and

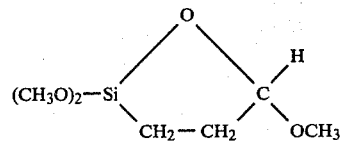

(the siloxa-cyclic). The hydroformylation of methylvinyldiethoxysilane produced as silane product mixture of

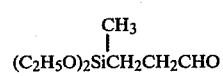
        CH₃
         |
(C₂H₅O)₂SiCH₂CH₂CHO (the normal isomer),

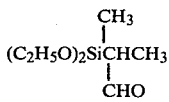

(the branch isomer) and

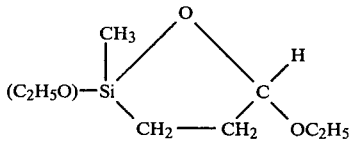

(the siloxa-cyclic). The catalyst employed in each example was activated 5% Rh/Al$_2$O$_3$ prepared as described in Example 1 added as 1:1 by weight with triphenylphosphite. A synthesis gas mixture of CO/H$_2$ in a 1:1 mole ratio was employed in each example. The remaining operating parameters and results are given in Table I below.

ture were the normal aldehyde isomer having the formula $(C_2H_5O)_3SiCH_2CH_2CH_2CHO$ and the branched aldehyde isomer having the formula

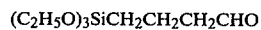

the two minor components comprising about 10% of the total liquid product mixture, also present in about a 1:1 ratio were siloxa-cyclic compounds having the formulas

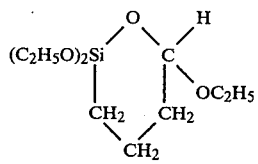

TABLE I

| Example No. | Vinyl Silane | Weight Grams | Catalyst Weight Grams | CO/H$_2$ Pressure (psig) | Temp. °C. Peak Exotherm | Time Hours | Percent Conversion | Product Composition Weight Percent* | | |
|---|---|---|---|---|---|---|---|---|---|---|
| | | | | | | | | Normal Isomer | Branch Isomer | Siloxa-Cyclic |
| 4 | CH$_2$=CHSi(OC$_2$H$_5$)$_3$ | 150 | 0.75 | 200 | 80(105) | 3 | 100 | 84.6 | 2.3 | 13.0 |
| 5 | CH$_2$=CHSi(OCH$_3$)$_3$ | 148.0 | 0.75 | 200 | 94(110) | 1¾ | 97 | 85.7 | 3.3 | 11.0 |
| 6 | CH$_2$=CHSi(OCH$_3$)$_3$ | 148.0 | 0.75 | 200 | 80(95) | 3¼ | 97.5 | 66.0 | 11.4 | 22.6 |
| 7 | CH$_2$=CHSi(OCH$_3$)$_3$ | 148.0 | 0.75 | 200 | 105(132) | 2 | 98 | 82.9 | 3.7 | 13.4 |
| 8 | CH$_2$=CHSi(OC$_2$H$_5$)$_3$ | 600.0 | 3.0 | 200 | 60(90) | 10 | 82 | 77.6 | 13.6 | 8.8 |
| 9 | CH$_2$=CHSi(OC$_2$H$_5$)$_3$ | 150.0 | 0.75 | 180 | 80(101) | 2 | 100 | 79.1 | 6.1 | 14.8 |
| 10 | CH$_2$=CHSi(OCH$_3$)$_3$ | 444.0 | 2.5 | 250 | 90(110) | 17 | 98 | 93.3 | 6.2 | 0.5 |
| 11 | CH$_2$=CHSi(OCH$_3$)$_3$ | 148.0 | 0.75 | 400 | 90(103) | 2 | 98 | 58.2 | 11.4 | 30.4 |
| 12 | CH$_2$=CHSi(OC$_2$H$_5$)$_3$ | 190.0 | 0.95 | 100 | 90(110) | 3½ | 97 | 76.6 | 15.8 | 7.6 |
| 13 | CH$_2$=CHSi(OC$_2$H$_5$)$_3$ | 190.0 | 0.95 | 400 | 85(100) | 2 | 98 | 71.2 | 5.8 | 22.9 |
| 14 | CH$_2$=CHSi(OCH$_3$)$_3$ | 148.0 | 0.75 | 200 | 100(115) | 2 | 98 | 79.0 | 4.2 | 16.8 |
| 15[a] | CH$_2$=CHSi(OCH$_2$)$_3$ | 148.0 | 0.75 | 200 | 100(115) | 3 | 96 | 67.5 | 18.2 | 14.3 |
| 16[b] | CH$_2$=CHSi(OCH$_3$)$_3$ | 148.0 | 0.75 | 200 | 100(105) | 4½ | 89 | 84.5 | 5.6 | 9.9 |
| 17[c] | CH$_2$=CHSi(OCH$_3$)$_3$ | 148.0 | 0.75 | 200 | 100(105) | 2½ | 88 | 92.5 | 3.3 | 4.2 |
| 18 | CH$_2$=CHSi(OCH$_3$)$_3$ | 222.0 | 1.125 | 200 | 100(105) | 3 | 97 | 77.2 | 9.3 | 13.5 |
| 19 | CH$_2$=CHSi(OCH$_3$)$_3$ | 222.0 | 1.125 | 400 | 100(105) | 2 | 97 | 69.3 | 6.7 | 24.0 |
| 20 | CH$_2$=CHSi(OCH$_3$)$_3$ | 222.0 | 1.125 | 100 | 100(120) | 6 | 95 | 87.2 | 4.0 | 8.8 |
| 21 | CH$_2$=CHSi(OCH$_3$)$_3$ | 190.0 | 0.95 | 400 | 100(110) | 1½ | 95 | 79.4 | 7.6 | 13.0 |
| 22[d] | CH$_2$=CHSi(OC$_2$H$_5$)$_3$ | 500.0 | 2.5 | 250 | 90(110) | 2 | 98 | 84.5 | — | 15.5 |
| 23 | CH$_2$=CHSi(OC$_2$H$_5$)$_3$ | 380.0 | 1.90 | 400 | 100(105) | 2½ | 100 | 79.9 | 13.2 | 6.9 |
| 24 | CH$_2$=CHSi(OC$_2$H$_5$)$_3$ | 380.0 | 1.90 | 400 | 100(105) | 3 | 100 | 80.0 | 13.0 | 7.0 |
| 25 | CH$_2$=CHSi(OC$_2$H$_5$)$_3$ | 150.0 | 0.75 | 250 | 110(130) | 1 | 93 | 84.1 | 3.0 | 12.9 |
| 26 | CH$_2$=CHSi(OC$_2$H$_5$)$_3$ | 150.0 | 0.75 | 250 | 110(125) | 2 | 100 | 88.1 | 2.3 | 9.6 |
| 27 | CH$_2$=CHSi(OC$_2$H$_5$)$_3$ | 500.0 | 2.5 | 250 | 90(110) | 2½ | 100 | 83.0 | 1.2 | 15.8 |
| 28 | CH$_2$=CHSi(OC$_2$H$_5$)$_3$ | 500.0 | 2.5 | 250 | 90(110) | 2 | 100 | 83.6 | 1.5 | 16.2 |
| 29 | CH$_2$=CHSi(OC$_2$H$_5$)$_2$<br>    |<br>    CH$_3$ | 160.0 | 0.75 | 200 | 90(105) | 2 | 100 | 78.9 | 4.7 | 16.4 |

[a]Contains 117 g trimethyl orthoformate (TMOF) as solvent.
[b]Contains 117 g TMOF and 35 g methanol (MeOH) as solvent.
[c]Contains 35 g MeOH as solvent.
[d]Run as 50 wt. % vinylsilane in ethanol.
*Gas chromatography analysis normalized to 100 percent conversion.

EXAMPLE 30

Following a procedure similar to Example 1, 61.6 g (0.30 mole) allyltriethoxysilane was hydroformylated with a 1:1 mixture of carbon monoxide-hydrogen at 250 psi pressure in the presence of 0.3 g of activated 5% Rh/Al$_2$O$_3$ catalyst prepared as described in Example 1 and 0.3 g triphenylphosphite at 100° C.+110° C. for 2½ hours. Product analysis by gas chromatography indicated total conversion of allyltriethoxysilane to four components: the two major components in about a 1:1 ratio being about 90% of the total liquid product mixture were the normal aldehyde isomer having the formula and

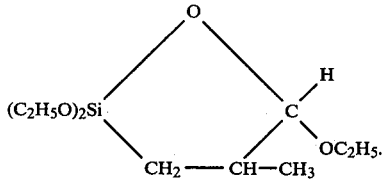

Infrared analysis of the total liquid product mixture showed a —C═O absorption at 5.80 microns. Proton nuclear magnetic resonance spectroscopy identified two aldehydic proton resonances (multiplets) at 9.65 and 9.78 ppm downfield from tetramethylsilane in approximately a 1:1 ratio.

EXAMPLE 31

Following the procedure of Example 1, 125 g (0.5 mole) of 3-methacryloxypropyltrimethoxysilane, 0.6 grams of activated 5% Rh/Al$_2$O$_3$ catalyst prepared as described in Example 1 and 0.6 g triphenylphosphite were placed in a 300 cc stainless steel autoclave. After purging the air, the reactor was pressurized to 250 psi with a 1:1 mixture of carbon monoxide and hydrogen. The autoclave was heated with rocking to 100° C. whereupon an exothermic reaction ensued which increased the temperature inside the reactor to 108° C. with concomitant pressure drop. After four hours reaction time, the reactor was cooled, vented and the liquid reaction product, filtered of catalyst residues, analyzed. Gas chromatograph analysis indicated 97% conversion of the silane starting material into two components in a 30:70 weight ratio. Infrared analysis showed two carbonyl abosrptions at 5.75 and 5.79 microns. Proton nuclear magnetic resonance indicated two aldehyde hydrogen absorbances at 9.69 (singlet) and 9.79 (triplet) ppm downfield from a tetramethylsilane reference, a 30:70 molar ratio. Based on the singlet aldehyde proton resonance the 30% component was

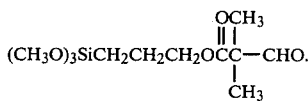

The 70% component was

as shown by the triplet aldehyde resonance. Both components had a molecular ion at mass 278 as analyzed by gas chromatography/mass spectroscopy.

EXAMPLE 32

A 50% solution of the aldehyde containing silane liquid reaction product mixture of Example 25 (distilled at 40° C. and 0.4 mm Hg.) in 95% ethanol (5% water) was prepared and 5 microscope slides were treated with the solution, allowed to air dry, then oven dried for 30 minutes at 105° C. Said five aldehyde functional silane treated slides and five untreated slides were then coated with a 20% solution of Plyophen 23-900 (Reichhold Chemical Co.) phenolic resin in ethanol. The slides were allowed to air dry 15 minutes, then were oven cured for one hour at 177° C. After cooling, the slides were immersed in boiling water for one hour. The slides were removed from the boiling water and cooled. Two of the untreated slides had no phenolic resin film remaining and the remaining three untreated ones had only a partial film. With all of the slides pre-treated with the aldehyde functional silane solution, resin film remained bonded to the glass.

Various modifications and variations of this invention will be obvious to a worker skilled in the art and it is to be understood that such modifications and variations are to be included within the purview of this application and the spirit and scope of the appended claims.

I claim:
1. A monoaldehyde containing hydrolyzable silane having the formula

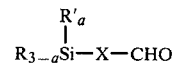

wherein R represents an alkoxy radical having from 1 to 4 carbon atoms, R' represents a monovalent alkyl radical having from 1 to 4 carbon atoms, X represents a divalent organic bridging group and a has a value of 0 to 2.

2. A monoaldehyde containing hydrolyzable silane having the formula:

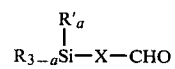

wherein R represents a methoxy or ethoxy radical; and wherein X represents a divalent organic radical containing from 2 to 8 carbon atoms selected from the group consisting of alkylene, alkylene-O-alkylene,

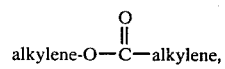

and cycloalkylene radicals.

3. A silane as defined in claim 2, wherein R' represents a methyl radical and a has a value or 0 or 1.

4. A silane as defined in claim 3, wherein X represents an ethylene radical having the formula —CH$_2$CH$_2$— or

5. A silane as defined in claim 3, wherein X represents a propylene radical having the formula —CH$_2$CH$_2$CH$_2$— or —CH$_2$CHCH$_3$.

6. A monoaldehyde containing hydrolyzable silane having the formula:

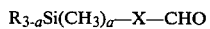

wherein R represents either a methoxy or ethoxy radical, "a" has a value of 0 to 1, and X represents a radical selected from the group consisting of:

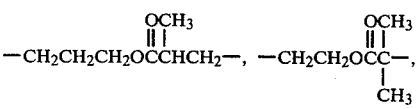

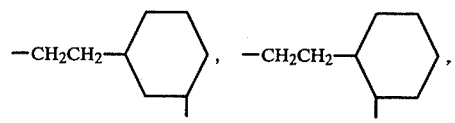

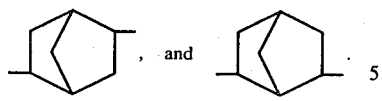

7. A silane as defined in claim 6, wherein X represents a cyclohexylene radical

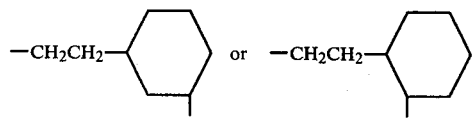

8. A silane as defined in claim 6, wherein X represents a bicycloheptene radical having the formula

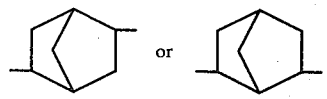

9. A silane as defined in claim 2, wherein R is a methoxy radical, X is a —CH$_2$CH$_2$— radical and a is 0.

10. A silane as defined in claim 2, wherein R is an ethoxy radical, X is a —CH$_2$CH$_2$— radical and a is 0.

11. A silane as defined in claim 2, wherein R is a methoxy radical, X is a —CH$_2$CH$_2$CH$_2$— radical and a is 0.

12. A silane as defined in claim 2, wherein R is an ethoxy radical, X is a

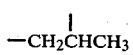

radical and a is 0.

13. A silane as defined in claim 2, wherein R is a methoxy radical, R' is a methyl radical, X is a —CH$_2$CH$_2$— radical and a is 1.

14. A silane as defined in claim 2, wherein R is an ethoxy radical, R' is a methyl radical, X is a —CH$_2$CH$_2$— radical and a is 1.

15. A silane as defined in claim 2, wherein R is a methoxy radical, R' is a methyl radical, X is a —CH$_2$CH$_2$CH$_2$— radical and a is 1.

16. A silane as defined in claim 2, wherein R is an ethoxy radical, R' is a methyl radical, X is a —CH$_2$CH$_2$CH$_2$— radical and a is 1.

17. A silane as defined in claim 2, wherein R is a methoxy radical, X is a

radical and a is 0.

18. A silane as defined in claim 2, wherein R is an ethoxy radical, X is a

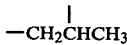

radical and a is 0.

19. A silane as defined in claim 2, wherein R is a methoxy radical, X is a

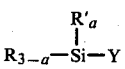

radical and a is 0.

20. A process for producing aldehyde containing hydrolyzable silanes as defined in claim 1, which comprises hydroformylating a hydrolyzable silane having the formula $$R_{3-a}-\underset{\underset{R'_a}{|}}{Si}-Y$$

wherein R, R' and a are the same as defined in claim 1, and Y represents an ethylenically unsaturated organic radical, with carbon monoxide and hydrogen in the presence of a Group VIII transition metal complex hydroformylation catalyst.

21. A process as defined in claim 20, wherein said catalyst is a rhodium complex hydroformylation catalyst; wherein R represents a methoxy or ethoxy radical and wherein X represents a divalent organic radical containing from 2 to 8 carbon atoms selected from the group consisting of alkylene, alkylene-O-alkylene,

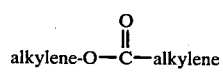

and cycloalkylene radicals.

22. A process as defined in claim 21, wherein R' represents a methyl radical and a has a value of 0 or 1.

23. A process as defined in claim 22, wherein X represents an ethylene radical having the formula —CH$_2$CH$_2$ or

24. A process as defined in claim 22, wherein X represents a propylene radical having the formula —CH$_2$CH$_2$CH$_2$— or

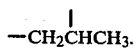

25. A silane as defined in claim 6, wherein X represents a radical having the formula

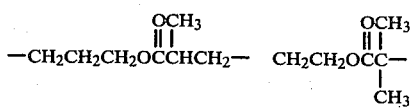

* * * * *

UNITED STATES PATENT AND TRADEMARK OFFICE
CERTIFICATE OF CORRECTION

PATENT NO. : 4,424,392

DATED : January 3, 1984

INVENTOR(S) : H. E. Petty

It is certified that error appears in the above-identified patent and that said Letters Patent is hereby corrected as shown below:

In column 4, line 38 the formula reading "$-CH_2CH_2C(CH_3)\ CH_2-$", should read -- $-CH_2CH_2C(CH_3)_2CH_2-$ --.

In column 13, line 56, the term "ollected" should read

--collected--.

In claim 3, second line, the phrase "a value or o or 1,"

should read -- a value of 0 or 1.--.

In claim 5, third line, the formula reading "$-CH_2CHCH_3$."

should read -- $-CH_2 \overset{|}{C}HCH_3$. --

In claim 23, third line, the formula reading "$-CH_2CH_2$"

should read -- $-CH_2CH_2-$ --.

*Signed and Sealed this*

*Second* Day of *July 1985*

[SEAL]

Attest:

DONALD J. QUIGG

*Attesting Officer*   *Acting Commissioner of Patents and Trademarks*